(12) United States Patent
Fujiwara et al.

(10) Patent No.: US 9,314,968 B2
(45) Date of Patent: Apr. 19, 2016

(54) PRESSING APPARATUS ASSOCIATED WITH AN ABSORBENT ARTICLE, AND PRESSING METHOD

(75) Inventors: Tomohiro Fujiwara, Kagawa (JP); Osamu Ishikawa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 147 days.

(21) Appl. No.: 13/819,721

(22) PCT Filed: Aug. 22, 2011

(86) PCT No.: PCT/JP2011/068843
§ 371 (c)(1),
(2), (4) Date: May 10, 2013

(87) PCT Pub. No.: WO2012/029573
PCT Pub. Date: Mar. 8, 2012

(65) Prior Publication Data
US 2013/0220541 A1    Aug. 29, 2013

(30) Foreign Application Priority Data
Aug. 31, 2010   (JP) .................................. 2010-194485

(51) Int. Cl.
*B29C 65/00*      (2006.01)
*B29C 43/28*      (2006.01)
(Continued)

(52) U.S. Cl.
CPC ..... *B29C 66/91631* (2013.01); *A61F 13/15699* (2013.01); *A61F 13/15739* (2013.01);
(Continued)

(58) Field of Classification Search
CPC .................... B29C 65/4815; B29C 66/83413; B29C 66/91631; A61F 13/15699
USPC ........ 156/324, 582, 555, 583.1; 604/365, 366
See application file for complete search history.

(56) References Cited

U.S. PATENT DOCUMENTS 3,484,325 A * 12/1969 Pendleton ..................... 156/582
4,610,042 A    9/1986 Theodorsen
(Continued)

FOREIGN PATENT DOCUMENTS

AU    2009324277 A1    8/2010
CN        1860075 A    11/2006
(Continued)

OTHER PUBLICATIONS

International Search Report from corresponding PCT application No. PCT/JP2011/068843 dated Oct. 11, 2011 (2 pgs).
(Continued)

*Primary Examiner* — John Goff
(74) *Attorney, Agent, or Firm* — Brinks Gilson & Lione

(57) ABSTRACT

A pressing apparatus associated with an absorbent article, including: a pair of rollers that are driven and rotate with outer circumferential surfaces thereof facing each other, when a fibrous continuous sheet overlapped with an article to be overlapped with a thermoplastic adhesive therebetween is passed in a continuous direction of the fibrous continuous sheet through a roller gap between the pair of rollers, the pressing apparatus sandwiching and pressing the article to be overlapped and the fibrous continuous sheet between the outer circumferential surfaces, and a heating mechanism that heats at least a roller of the pair of rollers that is positioned on a side of the fibrous continuous sheet, the heating mechanism heating the roller so as to keep a temperature of the outer circumferential surface of the roller within a range from 70° C. to 120° C.

3 Claims, 4 Drawing Sheets

(51) Int. Cl.
| | |
|---|---|
| *B29C 43/30* | (2006.01) |
| *B29C 65/18* | (2006.01) |
| *B29C 65/48* | (2006.01) |
| *B29C 65/52* | (2006.01) |
| *B32B 37/22* | (2006.01) |
| *B65H 37/04* | (2006.01) |
| *B32B 37/10* | (2006.01) |
| *B29C 65/30* | (2006.01) |
| *B32B 37/06* | (2006.01) |
| *A61F 13/15* | (2006.01) |
| *B29L 31/48* | (2006.01) |
| *B32B 37/12* | (2006.01) |

(52) U.S. Cl.
CPC ............... *B29C43/28* (2013.01); *B29C 43/30* (2013.01); *B29C 65/18* (2013.01); *B29C 65/305* (2013.01); *B29C 65/4815* (2013.01); *B29C 65/524* (2013.01); *B29C 66/43* (2013.01); *B29C 66/433* (2013.01); *B29C 66/472* (2013.01); *B29C 66/7294* (2013.01); *B29C 66/83413* (2013.01); *B29C 66/83415* (2013.01); *B29C 66/919* (2013.01); *B29C 66/91231* (2013.01); *B29C 66/91421* (2013.01); *B29C 66/91431* (2013.01); *B29C 66/91641* (2013.01); *B29C 66/961* (2013.01); *B32B 37/06* (2013.01); *B32B 37/10* (2013.01); *B32B 37/22* (2013.01); *B65H 37/04* (2013.01); *B29C 65/526* (2013.01); *B29C 66/45* (2013.01); *B29C 66/91216* (2013.01); *B29C 66/91651* (2013.01); *B29C 66/93451* (2013.01); *B29L 2031/4878* (2013.01); *B32B 37/12* (2013.01); *B32B 2037/1215* (2013.01); *B32B 2309/02* (2013.01); *B32B 2309/72* (2013.01); *B32B 2555/02* (2013.01); *B65H 2301/43822* (2013.01)

(56) References Cited

U.S. PATENT DOCUMENTS

| | | | | |
|---|---|---|---|---|
| 4,643,730 | A | * | 2/1987 | Chen et al. .................... 604/390 |
| 4,902,565 | A | * | 2/1990 | Brook ......................... 428/315.5 |
| 5,947,944 | A | * | 9/1999 | Hetzler et al. ................. 604/366 |
| 2005/0022925 | A1 | * | 2/2005 | Janssen ......................... 156/230 |
| 2006/0165886 | A1 | * | 7/2006 | Werenicz et al. ........... 427/208.2 |

FOREIGN PATENT DOCUMENTS

| | | | |
|---|---|---|---|
| EP | 1 065 047 | A1 | 1/2001 |
| JP | 51-81491 | A | 7/1976 |
| JP | 10-323368 | A | 12/1998 |
| JP | 2001-9960 | A | 1/2001 |
| JP | 2005-218648 | A | 8/2005 |
| WO | WO 2011-118725 | A1 | 9/2011 |

OTHER PUBLICATIONS

Chinese First Office Action and English translation from corresponding Chinese application No. 201180041785.1 dated May 27, 2014 (12 pgs).

European extended Search Report from corresponding European application No. 11821590.4 dated Jun. 16, 2014 (5 pgs).

Japanese Official Action from corresponding Japanese application No. 2010-194485 dated Apr. 4, 2014.

European Office Action from European application No. 11821590.4 dated Jul. 14, 2015 (3 pgs).

* cited by examiner

PRESSING APPARATUS ASSOCIATED WITH AN ABSORBENT ARTICLE, AND PRESSING METHOD

RELATED APPLICATION

The present application is a 35 U.S.C. §371 national stage filing of International Patent Application No. PCT/JP2011/068843, filed Aug. 22, 2011, to which priority is claimed under 35 U.S.C. §120 and through which priority is claimed under 35 U.S.C. §119 to Japanese Priority Patent Application No. 2010-194485, filed Aug. 31, 2010.

TECHNICAL FIELD

The present invention relates to a pressing apparatus associated with an absorbent article such as a disposable diaper, and a pressing method.

BACKGROUND ART

In a conventional manufacturing line of an absorbent article such as a disposable diaper, as shown in FIG. 1, a semi-finished product 2 is manufactured in such a manner that each of absorbent bodies 3, 3 . . . formed by shaping pulp fiber are covered from above and below with fibrous continuous sheets 6, 4 such as a pair of tissue papers.

Then, this semi-finished product 2 is cut at a product pitch to be used as disposable diapers (PTL 1).

CITATION LIST

Patent Literature

[PTL 1]
Japanese Patent Application Laid-open No. 2001-9960

SUMMARY OF THE INVENTION

Technical Problem

With such a semi-finished product 2, in order to integrate an absorbent body 3 with a pair of upper and lower fibrous continuous sheets 6, 4, a hot-melt adhesive (not shown) is applied on one surface of the two surfaces of a fibrous continuous sheet 4 which is on the side facing the other fibrous continuous sheet 6. Therefore, these three are made to be adhesively integrated. In the manufacturing line, in order to increase the degree of integration or to reduce the thickness of the semi-finished product 2, the semi-finished product 2 is passed through a roller gap Gr between a pair of upper and lower press rollers 12, 12, and is sandwiched and pressed between the outer circumferential surfaces 12s, 12s of the press rollers 12, 12 when being passed therethrough.

However, when the semi-finished product 2 is sandwiched and pressed, there is a risk that the hot-melt adhesive oozes out to the outer surfaces of the fibrous continuous sheets 6, 4 through spaces between fibers of the fibrous continuous sheets 6, 4, to adhere to the outer circumferential surface 12s of the press roller 12 making the outer circumferential surface dirty. Therefore, the press roller 12 needs to be cleaned up regularly.

Furthermore, when this adhesive is deposited on the outer circumferential surface 12s of the press roller 12, the fibrous continuous sheets 6, 4 stick tightly on the outer circumferential surface 12s of the press roller 12 due to the adhesive strength of the adhesive. Then, in the case that these stuck fibrous continuous sheets 6, 4 are not quickly pulled off from the outer circumferential surface 12s at the exit side of the roller gap Gr, the fibrous continuous sheets 6, 4 would be torn. Consequently, it is inevitable to stop the manufacturing line.

The present invention has been made in view of the conventional problems described above, and an advantage thereof is to reduce the occurrence of situations in which the adhesive adheres to the outer circumferential surface of the roller, and the fibrous continuous sheet sticks to the outer circumferential surface thereof.

Solution to Problem

A principal aspect of the present invention for achieving the above advantage is, A pressing apparatus associated with an absorbent article, including:

a pair of rollers that are driven and rotate with outer circumferential surfaces thereof facing each other, when a fibrous continuous sheet overlapped with an article to be overlapped with a thermoplastic adhesive therebetween is passed in a continuous direction of the fibrous continuous sheet through a roller gap between the pair of rollers, the pressing apparatus sandwiching and pressing the article to be overlapped and the fibrous continuous sheet between the outer circumferential surfaces, and a heating mechanism that heats at least a roller of the pair of rollers that is positioned on a side of the fibrous continuous sheet, the heating mechanism heating the roller so as to keep a temperature of the outer circumferential surface of the roller within a range from 70° C. to 120° C.

Moreover,

A pressing method associated with an absorbent article in which when a fibrous continuous sheet overlapped by an article to be overlapped with a thermoplastic adhesive therebetween is passed in a continuous direction of the fibrous continuous sheet through a roller gap between a pair of rollers that are driven and rotate with outer circumferential surfaces thereof facing each other, the article to be overlapped and the fibrous continuous sheet are sandwiched and pressed between the outer circumferential surfaces, comprising:

heating at least a roller of the pair of rollers that is positioned on a side of the fibrous continuous sheet so as to keep a temperature of the outer circumferential surface of the roller within a range from 70° C. to 120° C.; and sandwiching and pressing the article to be overlapped and the fibrous continuous sheet passing through the roller gap between the outer circumferential surfaces of the rollers, the temperature of the outer circumferential surface of the roller being kept within the range.

Other features of the present invention will become apparent from the description in this specification and the attached drawings.

Effects of the Invention

According to the present invention, it is possible to reduce the occurrence of situations in which the adhesive adheres to the outer circumferential surface of the roller, and the fibrous continuous sheet sticks to the outer circumferential surface thereof.

MODE FOR CARRYING OUT THE INVENTION

Figure 1:
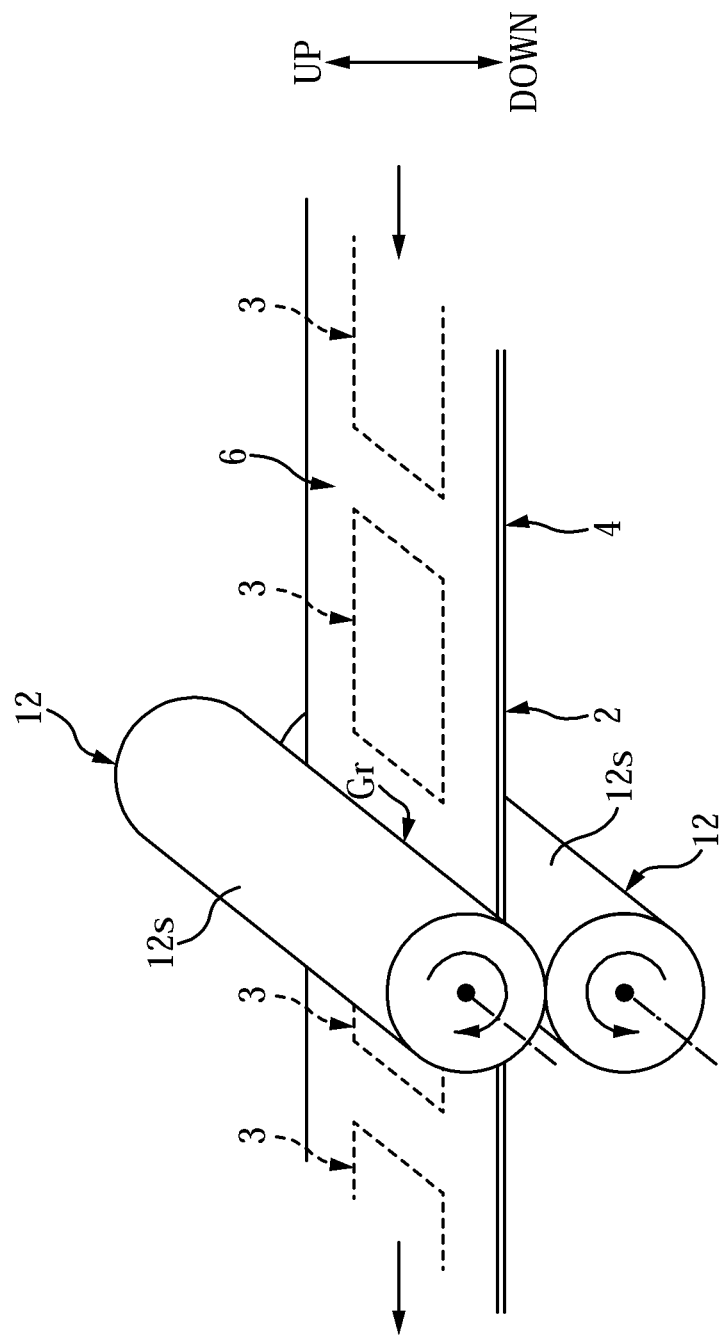
FIG. 1 is a schematic perspective view of a conventional pressing apparatus.

At least the following matters will be made clear by the description in the present specification and the accompanying drawings.

A pressing apparatus associated with an absorbent article, including:

a pair of rollers that are driven and rotate with outer circumferential surfaces thereof facing each other, when a fibrous continuous sheet overlapped with an article to be overlapped with a thermoplastic adhesive therebetween is passed in a continuous direction of the fibrous continuous sheet through a roller gap between the pair of rollers, the pressing apparatus sandwiching and pressing the article to be overlapped and the fibrous continuous sheet between the outer circumferential surfaces, and a heating mechanism that heats at least a roller of the pair of rollers that is positioned on a side of the fibrous continuous sheet, the heating mechanism heating the roller so as to keep a temperature of the outer circumferential surface of the roller within a range from 70° C. to 120° C.

With such a pressing apparatus associated with an absorbent article, during sandwiching and pressing, the temperature of the outer circumferential surface of the roller that comes into contact with the fibrous continuous sheet is kept within a range from 70° C. to 120° C. Therefore, even if the adhesive passes through a space between fibers of the fibrous continuous sheet and oozes out to the outer circumferential surface, the adhesion of the adhesive to the outer circumferential surface and the sticking of the fibrous continuous sheet to the outer circumferential surface can be effectively suppressed.

In such a pressing apparatus associated with an absorbent article, it is desirable that the temperature of the outer circumferential surface is kept within a range from 80° C. to 110° C.

With such a pressing apparatus associated with an absorbent article, during sandwiching and pressing, the temperature of the outer circumferential surface of the roller that comes into contact with the fibrous continuous sheet is kept within a range from 80° C. to 110° C. Therefore, even if the adhesive oozes out to the outer circumferential surface, the adhesion of the adhesive to the outer circumferential surface and the sticking of the fibrous continuous sheet to the outer circumferential surface can be effectively suppressed.

In such a pressing apparatus associated with an absorbent article, it is desirable that the thermoplastic adhesive is a hot-melt adhesive, and the fibrous continuous sheet is tissue paper.

With such a pressing apparatus associated with an absorbent article, the above-mentioned suppressing effect can be effectively obtained.

In such a pressing apparatus associated with an absorbent article, it is desirable that, an absorbent body associated with the absorbent article is placed intermittently on the fibrous continuous sheet in the continuous direction of the fibrous continuous sheet, when the fibrous continuous sheet is a first fibrous continuous sheet, the absorbent body is covered with a second fibrous continuous sheet, to thereby sandwich the absorbent body between the second fibrous continuous sheet and the first fibrous continuous sheet, and the heating mechanism heats both of the pair of rollers, and thereby keeping the temperatures of the outer circumferential surfaces of both of the rollers within a range from 70° C. to 120° C.

With such a pressing apparatus associated with an absorbent article, there is a risk that the adhesive oozes out to each of the outer surfaces of the first fibrous continuous sheet and the second fibrous continuous sheet. In this regard, the temperature of the outer circumferential surface of each roller is kept within a range from 70° C. to 120° C. Therefore, the adhesion of the adhesive to the outer circumferential surface and the sticking of the fibrous continuous sheet to the outer circumferential surface can be effectively suppressed.

Furthermore, A pressing method associated with an absorbent article in which when a fibrous continuous sheet overlapped by an article to be overlapped with a thermoplastic adhesive therebetween is passed in a continuous direction of the fibrous continuous sheet through a roller gap between a pair of rollers that are driven and rotate with outer circumferential surfaces thereof facing each other, the article to be overlapped and the fibrous continuous sheet are sandwiched and pressed between the outer circumferential surfaces, including:

heating at least a roller of the pair of rollers that is positioned on a side of the fibrous continuous sheet so as to keep a temperature of the outer circumferential surface of the roller within a range from 70° C. to 120° C.; and sandwiching and pressing the article to be overlapped and the fibrous continuous sheet passing through the roller gap between the outer circumferential surfaces of the rollers, the temperature of the outer circumferential surface of the roller being kept within the range.

With such a pressing method associated with an absorbent article, during sandwiching and pressing, the temperature of the outer circumferential surface of the roller that comes into contact with the fibrous continuous sheet is kept within a range from 70° C. to 120° C. Therefore, even if the adhesive passes through the spaces between fibers of the fibrous continuous sheet and oozes out to the outer circumferential surface, the adhesion of the adhesive to the outer circumferential surface and the sticking of the fibrous continuous sheet to the outer circumferential surface can be effectively suppressed.

Present Embodiment

Figure 2A:
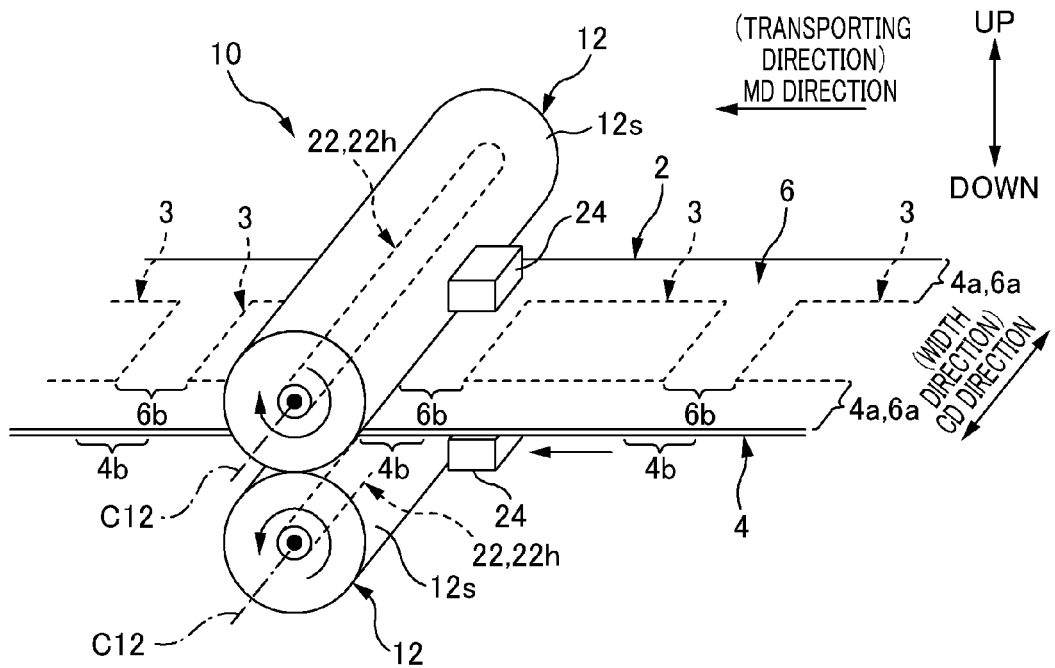
FIG. 2A is a schematic perspective view of a pressing apparatus 10 of the present embodiment.
Figure 2B:
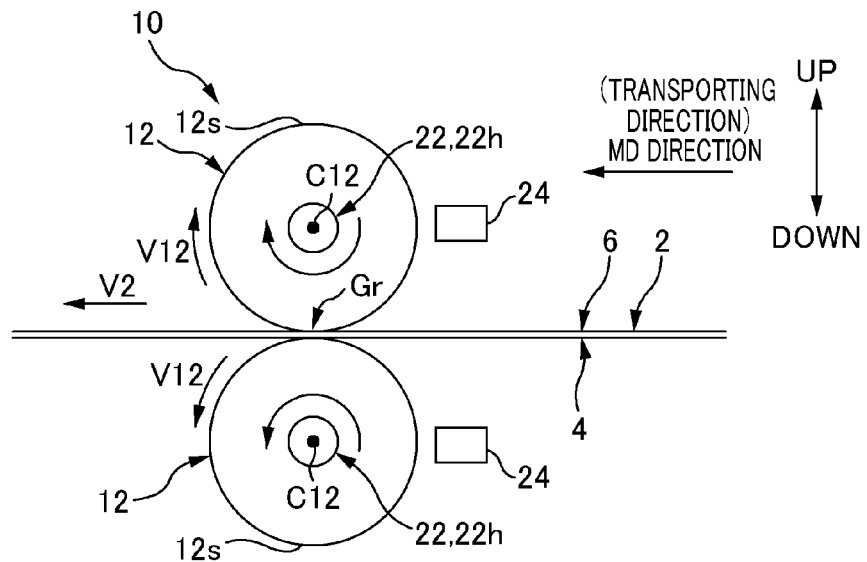
FIG. 2B is a schematic side view of a pressing apparatus 10 of the present embodiment.

FIGS. 2A and 2B are explanatory views of a pressing apparatus 10 of the present embodiment. FIG. 2A is a schematic perspective view of the pressing apparatus 10, and FIG. 2B is a schematic side view thereof. Note that, the absorbent body 3 of the semi-finished product 2 is not shown in FIG. 2B.

This pressing apparatus 10 is used in a manufacturing line of disposable diapers as an example of the absorbent article. In the pressing apparatus 10, semi-finished products 2 of diapers, for example, are continuously supplied in a transporting direction, and the pressing apparatus 10 sandwiches and presses these semi-finished products 2 in a thickness direction and forwards the semi-finished products 2 to the downstream process.

The semi-finished product 2 includes, for example, a first fibrous continuous sheet 4 that is continuously transported in the transporting direction, a plurality of absorbent bodies 3, 3 . . . , as a example of articles to be overlapped intermittently at a product pitch in the transporting direction on the first fibrous continuous sheet 4, and a second fibrous continuous sheet 6 that covers the absorbent bodies 3, 3 . . . from above so as to sandwich the absorbent bodies 3, 3 . . . between the first fibrous continuous sheet 4 and the second fibrous continuous sheet 6.

The absorbent body 3 is formed by layering pulp fiber that is as a fluid-absorbent fiber having, for example, a basis weight of 100 to 400 (g/m$^2$) to be a certain shape such as a substantially rectangular parallelepiped. Typically, superabsorbent polymer (hereinafter, referred to also as SAP) is mixed in this absorbent body 3. However, SAP does not have to be mixed therein. In this example, SAP is mixed to have a basis weight of 50 to 300 (g/m$^2$).

Nonwoven fabric or the like can be given as an example of the first and the second fibrous continuous sheets 4, 6. More specifically, a wet nonwoven fabric such as tissue paper including wood pulp fiber, and a dry nonwoven fabric including synthetic fiber with short fiber and semisynthetic fiber such as rayon can be given as an example. Note that, the wet nonwoven fabric means a nonwoven fabric on which bonding is performed after forming on a wire net that is in a fiber dispersed liquid. The dry nonwoven fabric means a nonwoven fabric on which the bonding is performed after a fibrous web is formed by a carding machine. In this example, tissue paper having a basis weight of 12 to 20 (g/m$^2$), which is made of wood pulp fiber, is used for each of the first and the second fibrous continuous sheets 4, 6. The tensile strength in the transporting direction of this tissue paper is 5 to 10 (N/25 mm), and that in the width direction is 1 to 5 (N/mm). Furthermore, the description of "25 mm" in the denominator associated with the unit of the former tensile strength indicates that the indicated value of the tensile strength is the tensile strength per width of 25 mm.

With regard to the fibrous continuous sheet 4 (6) that is at least one of the pair of upper and lower fibrous continuous sheets 6, 4, on one surface of the two surfaces of the fibrous continuous sheet 4 (6), that is on the side facing the absorbent body 3, hot-melt adhesive as the thermoplastic adhesive has been applied in advance over substantially the entire surface with a predetermined application pattern (for example, a plurality of wavy line patterns along the transporting direction). Therefore, based on the adhesive strength of the adhesive, the absorbent body 3, the first fibrous continuous sheet 4, and the second fibrous continuous sheet 6 are joined together.

For example, in the case where the object of application is the first fibrous continuous sheet 4, the adhesive is applied on an upper surface thereof before the absorbent bodies 3, 3 . . . are overlapped thereon. The absorbent body 3 is bonded to a portion of the first fibrous continuous sheet 4 on which the absorbent body 3 is overlapped. On the other hand, in a portion 4a that projects outside of the absorbent body 3 in the width direction and a portion 4b that is between adjacent absorbent bodies 3, 3 in the transporting direction, the second fibrous continuous sheet 6 comes into contact with the portions 4a and 4b and is bonded thereto. Thereby, the absorbent body 3 is sandwiched between the first fibrous continuous sheet 4 and the second fibrous continuous sheet 6, that is, these three are joined and integrated in such a state.

On the other hand, in the case where the object of application is the second fibrous continuous sheet 6, the adhesive is applied on the lower surface thereof before the second fibrous continuous sheet 6 is overlapped from above the first fibrous continuous sheet 4 on which the absorbent bodies 3, 3 . . . have been overlapped. Then, the absorbent body 3 is bonded to a portion of the second fibrous continuous sheet 6 on which the absorbent body 3 is overlapped. On the other hand, in a portion 6a that projects outside of the absorbent body 3 in the width direction and a portion 6b that is between adjacent absorbent bodies 3, 3 in the transporting direction, the first fibrous continuous sheet 4 comes into contact with the portions 6a and 6b and is bonded thereto. Thereby, the absorbent body 3 is sandwiched between the first fibrous continuous sheet 4 and the second fibrous continuous sheet 6, that is, these three are joined and integrated in such a state.

Examples of the hot-melt adhesive include a synthetic rubber type hot-melt adhesive (hot-melt adhesive having a base polymer of synthetic rubber such as SIS, SBS, SEPS, or SEBS), and a polyolefin type hot-melt adhesive (hot-melt adhesive having a base polymer of polyolefin such as PE, or PP). Here, MQ-654E (product name) (by Henkel Japan) is used. Furthermore, an application quantity per unit area of the adhesive is set to 2 to 10 (g/m$^2$). Moreover, the hot-melt adhesive is applied by being ejected from such as a nozzle of an appropriate adhesive application device. The temperature of the adhesive when ejected is increased to, for example, 140° C. to 160° C. by heating the adhesive, and the viscosity thereof is, for example, 2000 to 200000 (cP).

The pressing apparatus 10 is an apparatus that sandwiches and presses the semi-finished product 2 in the thickness direction in order to reduce the thickness of the semi-finished product 2 to the predetermined thickness. A compressive load associated with sandwiching and pressing the product is set to, for example, 35000 to 140000 (N/m) per unit width. During the sandwiching and pressing, the hot-melt adhesive is still unsolidified, that is, still has flowability. Therefore, the hot-melt adhesive is spread and smoothed over substantially the entire surface of the fibrous continuous sheets 4, 6 by the sandwiching and pressing, and the joining strength of the semi-finished product 2 can be increased as a whole.

A pressing apparatus 10 will be described below in detail. In the following description, the transporting direction of the semi-finished product 2 is also referred to as the "MD direction". Also, among the directions which are perpendicular to the MD direction, the width direction (the width direction of the fibrous continuous sheets 4, 6) of the semi-finished product 2 is also referred to the "CD direction". Note that, the CD direction is directed, for example, in a horizontal direction, and is directed in a direction perpendicular to the paper surface in FIG. 2B.

As shown in FIGS. 2A and 2B, the pressing apparatus 10 includes a pair of upper and lower press rollers 12, 12 that is driven and rotates with outer circumferential surfaces 12s, 12s facing each other, and a heating mechanism that heats each of the rollers 12, 12 so that the temperature of each of the outer circumferential surfaces 12s, 12s is within a range of the predetermined target temperature. Then, when the semi-finished product 2 is passed through a roller gap Gr between the press rollers 12, 12 along the MD direction, the semi-finished product 2 is sandwiched and pressed between these outer circumferential surfaces 12s, 12s while keeping the temperature of each of the outer circumferential surfaces 12s, 12s within a range from 70° C. to 120° C., that is a target temperature thereof.

Each of the press rollers 12 is, for example, a flat roller with a smooth outer circumferential surface 12s. These press rollers 12, 12 are rotatably supported around rotational shafts C12, C12 that are parallel to the CD direction by bearing members that are not shown, respectively. A drive torque is inputted from a motor that is not shown as a driving power source through such as a speed reducer, so that each of the press rollers 12 is driven and rotates along the MD direction. The circumferential velocity V12 of each of the press rollers 12 is changed in a range of 100 (m/min) to 600 (m/min) in conjunction with the transportation velocity V2 of the semi-finished product 2. More specifically, the pressing apparatus 10 has a speed control section (not shown) such as a computer or PLC (programmable logic controller), and the rotation of the motor is controlled by this speed control section. Therefore, each of the press rollers 12 is rotated while being synchronized with the transportation velocity V2 of the semi-finished product 2 so that the transportation velocity V2 and the circumferential velocity V12 are matched.

In this example, the press roller 12 is made of S45C (under JIS (Japan Industrial Standard)) steel. However, the material is not limited thereto. For example, the roller may be made of non-ferrous metal such as aluminum or copper. In the case that the roller has appropriate heat resistance or thermal conductivity, the roller may be made of non-metal material such as resin.

The heating mechanism is a device for suppressing the adhesion of the hot-melt adhesive to the outer circumferential surface 12s of the press roller 12 and the sticking of the fibrous continuous sheets 6, 4 to the outer circumferential surface 12s.

More specifically, in the above-mentioned semi-finished product 2 to be sandwiched and pressed by the upper and lower press rollers 12, 12, since the upper and lower continuous sheets 6, 4 which are upper and lower surfaces of the semi-finished product 2 are fibrous sheets as stated above, when sandwiching and pressing the semi-finished product 2, there is a possibility that the hot-melt adhesive inside the semi-finished product 2 oozes out to the upper and lower surfaces which are the outer surfaces of the sheets 6, 4, through the spaces between fibers of each of the fibrous continuous sheets 6, 4. Then, the oozed-out adhesive adheres to the outer circumferential surfaces 12s, 12s of the press rollers 12, 12 and makes the surfaces dirty. In some cases, the oozed-out adhesive is deposited on the outer circumferential surfaces 12s, 12s, and the fibrous continuous sheets 6, 4 stick to the outer circumferential surfaces 12s, 12s and are caught due to the adhesive action of the deposited adhesive. Consequently, the fibrous continuous sheets 6, 4 are torn. In this case, it is necessary to stop the manufacturing line and perform recovery operations such as removing the torn fibrous continuous sheets 6, 4 and cleaning the outer circumferential surfaces 12s, 12s. As a result, this reduces the productivity. Therefore, in order to suppress such adhesion of the hot-melt adhesive to the outer circumferential surface 12s of the press roller 12 and the sticking of the fibrous continuous sheets 6, to the outer circumferential surface, and to prevent the breakage of the sheets 6, 4, each of the press rollers 12 is heated, and the temperature of each of the outer circumferential surfaces 12s is kept within a range from 70° C. to 120° C. which a target temperature of the surface. Note that, the reasons why the adhesion of the adhesive and the sticking of the fibrous continuous sheets 6, 4 are suppressed and the breakage of the sheets 6, 4 is prevented by keeping the temperature within a range of the target temperature will be described later.

The heating mechanism with such a function includes a heating element 22 inserted into the inside of the press roller 12, a temperature sensor 24 that measures the temperature of the outer circumferential surface 12s of the press roller 12, and a temperature control section (not shown) that controls a heating value of the heating element 22 based on a temperature signal output from the temperature sensor 24.

The heating elements 22, 22 and the temperature sensors 24, 24 are provided for each of the press rollers 12 in relation to one another. The temperature control section controls the heating value of the corresponding heating element 22 based on the temperature signal of the temperature sensor 24 while relating each of the temperature sensors 24, 24 to each of the heating elements 22, 22 respectively. That is, the temperature signal of the temperature sensor 24 of the upper press roller 12 is provided to control the temperature of the heating element 22 in the upper press roller 12, and the temperature signal of the temperature sensor 24 of the lower press roller 12 is provided to control that of the heating element 22 in the lower press roller 12.

The heating element 22 is, for example, an electric heater, and produces heat based on supplied electric power. Supplying and stopping electric power is performed by a temperature control section. For example, when the indicated value of the temperature signal from the temperature sensor 24 becomes 85° C. or lower that is a first threshold being higher than 70° C. that is the lower limit value in the range of the target temperature, the temperature control section feeds electrical power to the heating element 22. On the other hand, when the indicated value of the temperature signal from the temperature sensor 24 becomes 105° C. or higher that is a second threshold being lower than 120° C. that is the upper limit value in the range of the target temperature and being higher than the first threshold, feeding of electrical power is stopped. Therefore, keeping the temperature of the outer circumferential surface 12s permanently within a range from 70 to 120° C., which is in the range of the above-mentioned target temperature, can be achieved. Note that, the temperature control section is, for example, a computer or PLC, and performs such a control action stated above by allowing a processor included in the section to read out an appropriate program from a memory and execute the program.

The position in which the heating element 22 is inserted is determined so as to be symmetrical about the rotational shaft C12 so that the outer circumferential surface 12s of the press roller 12 is equally heated over the whole circumference. Here, in each of the press rollers 12, one receiving hole 22h that receives the substantially stick-like heating element 22 along the rotational shaft C12 is formed so that the center of the hole 22h corresponds to the rotational shaft C12. However, the invention is not limited thereto. For example, each of a plurality of receiving holes may be formed in a position that is radially equidistant from the outer circumferential surface 12s and divides the entire circumference of the press roller 12 equally in a circumferential direction to receive the heating element 22 in each of the receiving holes.

As an example of the temperature sensor 24, a non-contact type temperature sensor is used in such a manner that the temperature of the outer circumferential surface 12s of the press roller 12 that is an object whose temperature is to be measured can be measured in a non-contact state with the outer circumferential surface 12s. As an example of such a non-contact type temperature sensor, there is a radiation thermometer or the like that measures temperature based on the amount of radiation of the object whose temperature is to be measured. Although the above thermometer is used here, the invention is not limited thereto. For example, a contact-type thermometer may be used. In other words, the temperature of the outer circumferential surface 12s may be measured by making a temperature detecting section such as a thermocouple come into sliding contact with the outer circumferential surface 12s of the press roller 12.

Here, the reasons why the adhesion of the hot-melt adhesive to the outer circumferential surface 12s of the press roller 12 and the sticking of the fibrous continuous sheet 4(6) to the outer circumferential surface 12s are suppressed and the breakage of the sheet 4(6) is prevented by keeping the temperature of the outer circumferential surface 12s within a range from 70° C. to 120° C. as mentioned above, will be described below.

Before that, the meanings of the terms used in the following explanation will be described. To "cohere" means that the adhesive forms lumps. "Cohesion failure" means that the adhesive that has cohered and formed a lump is taken apart, for example, by being pulled. "Anchor performance is high" means, for example, that it becomes difficult for the adhesive to leave the fibrous continuous sheet 4(6) because of the adhesive spreading to the spaces between fibers of the fibrous continuous sheet 4(6). In other words, the adhesive is trapped in the fibrous continuous sheet 4(6) and easily remains.

The above reasons will be described below by using these terms.

First, the temperature of the hot-melt adhesive falls to about 40° C. to 60° C. by the time the fibrous continuous sheet 4(6) has reached the roller gap Gr of the press roller 12. Therefore, the adhesive just before reaching the roller gap Gr is substantially in a cohesive state while adhering to the fiber of the fibrous continuous sheet 4(6).

Here, when the temperature of the outer circumferential surface 12s of the press roller 12 is higher than 120° C., the temperature of the outer circumferential surface 12s is much higher than the temperature of the adhesive. Due to this, when the adhesive of the fibrous continuous sheet 4(6) contacts the outer circumferential surface 12s, a great amount of heat is inputted into the adhesive from the outer circumferential surface 12s. Then, due to this great amount of inputted heat, the adhesive of the fibrous continuous sheet 4(6) is immediately softened and melted, and adheres to the outer circumferential surface 12s of the press roller 12 due to the occurrence of cohesion failure. As a result, a significant amount of adhesive is deposited relatively early on the outer circumferential surface 12s.

Then, the fibrous continuous sheet 4(6) is joined to the outer circumferential surface 12s via the deposited adhesive. Here, if this joining strength is much weaker than the tensile strength of the fibrous continuous sheet 4(6), the fibrous continuous sheet 4(6) is smoothly pulled off from the outer circumferential surface 12s due to transport tension imparted from the downstream process to the fibrous continuous sheet 4(6) at the exit side of the roller gap Gr. Therefore, the fibrous continuous sheet 4(6) is promptly transported to the downstream process without being torn.

However, when the temperature of the outer circumferential surface 12s is a high temperature such as 120° C. or higher mentioned above, a great amount of adhesive is deposited on the outer circumferential surface 12s based on the cohesion failure of the adhesive as stated above. Then, the adhesive strength of the adhesive increases as well, due to the great amount of deposited adhesive. More specifically, the fibrous continuous sheet 4(6) sticks to the outer circumferential surface 12s via the adhesive with high joining strength. Accordingly, even when the transport tension acts on the fibrous continuous sheet 4(6), the fibrous continuous sheet 4(6) keeps holding on without being pulled off from the outer circumferential surface 12s. On the other hand, here, since the fibrous continuous sheet is a collection of multiple fibers, the fibrous continuous sheet 4(6) can easily have a portion the strength of which is weaker than the above-mentioned joining strength. Therefore, finally, since the fibrous continuous sheet 4(6) will be torn starting from the weak portion, a part of the fibrous continuous sheet 4(6) is carried away by the press roller 12 while being stuck to the outer circumferential surface 12s, and the remaining portion thereof is transported to the downstream process. That is, the fibrous continuous sheet 4(6) breaks.

On the other hand, in the case that the temperature of the outer circumferential surface 12s of the press roller 12 is lower than 70° C., the amount of heat inputted into the adhesive becomes small at the time the outer circumferential surface 12s contacts the adhesive of the fibrous continuous sheet 4(6) because the temperature of the outer circumferential surface 12s is relatively low. Therefore, since the degree of softening and melting of the adhesive is low and the cohesion failure generally does not occur, the adhesion of the adhesive to the outer circumferential surface 12s due to the cohesion failure is suppressed.

However, when being sandwiched and pressed at the roller gap Gr, the adhesive is in a cohesive state and the flowability thereof is low. Therefore, the adhesive is tightly compressively-bonded on the outer circumferential surface 12s, and the fibrous continuous sheet 4(6) is tightly stuck to the outer circumferential surface 12s via the compressively-bonded adhesive.

Therefore, as in the above description, when an attempt is made to pull the fibrous continuous sheet 4(6) stuck to the outer circumferential surface 12s off from the outer circumferential surface 12s by transport tension at the exit side of the roller gap Gr, the sheet would be torn starting from the portion the strength of which is weak in the fibrous continuous sheet 4(6).

On the other hand, in the case that the temperature of the outer circumferential surface 12s of the press roller 12 is within a range from 70° C. to 120° C., the amount of inputted heat into the adhesive at the time that the outer circumferential surface 12s contacts the adhesive of the fibrous continuous sheet 4(6) would be a generally appropriate quantity. Due to this inputted heat, the adhesive will be having appropriate cohesion and flowability. Therefore, when the adhesive of the fibrous continuous sheet 4(6) contacts the outer circumferential surface 12s, a significant cohesion failure does not occur. Accordingly, the adhesion of the adhesive to the outer circumferential surface 12s is suppressed. Furthermore, since the adhesive has appropriate flowability, the adhesive promptly spreads to the inter-fiber empty space of the fibrous continuous sheet 4(6) when being sandwiched and pressed. This makes it easier for the adhesive to be held on the fibrous continuous sheet 4(6). That is, anchoring performance of the adhesive with respect to the fibrous continuous sheet 4(6) is improved. This also contributes to suppressing adhesion of the adhesive to the outer circumferential surface 12s. In addition, based on the above-mentioned appropriate flowability, the adhesive is flexibly deformed when being sandwiched and pressed. Therefore, it is also possible to suppress the tight compressive-bonding of the adhesive to the press roller 12.

As a result, it is possible to effectively avoid the fibrous continuous sheet 4(6) from being tightly stuck to the outer circumferential surface 12s. Consequently, the fibrous continuous sheet 4(6) is smoothly pulled off from the outer circumferential surface 12s of the press roller 12 due to transport tension that acts at the exit side of the roller gap Gr. Therefore, the breakage of the fibrous continuous sheet 4(6) can be prevented.

In order to ensure such effects, it is desirable that the temperature of the outer circumferential surface 12s of the press roller 12 is kept in a range from 80° C. to 110° C., which is a narrower range than the above-mentioned 70° C. to 120° C.

In the above-mentioned example, since both the upper and lower continuous sheets 6, 4 being upper and lower surfaces of the semi-finished product 2 are fibrous sheets, when the semi-finished product 2 is sandwiched and pressed between the upper and lower press rollers 12, 12, there was a risk of the hot-melt adhesive therein oozing out to each of the upper and lower surfaces of the semi-finished product 2. Therefore, although the upper and lower press rollers 12, 12 are heated so that the temperatures of both outer circumferential surfaces 12s, 12s thereof are to be from 70° C. to 120° C., if the hot-melt adhesive does not ooze out to one of the upper and lower surfaces of the semi-finished product 2, only the press roller 12 positioned at the side of the surface where the adhesive oozes out may be heated without heating the other press roller 12 positioned at the side of the surface where the adhesive does not oozes out.

For example, in the case that the continuous sheet 6 that is an upper surface in FIG. 2B is a fibrous sheet, and the continuous sheet 4 that is a lower surface therein is a fluid-impermeable sheet such as a film, the hot-melt adhesive does not ooze out from the lower surface of the semi-finished product 2. Therefore, in this case, the heating element 22 and the temperature sensor 24 is only needed to be provided to the upper press roller 12, and not for the lower press roller 12.

Moreover, in the foregoing descriptions, as an aspect of the semi-finished product 2, a product was exemplified in which the absorbent body 3 is interposed between a pair of upper and lower fibrous continuous sheets 6, 4. However, the aspect of the semi-finished product 2 is not limited thereto. For example, semi-finished products may also be used in which the absorbent body 3 is not interposed between a pair of upper and lower fibrous continuous sheets 6, 4, and the second fibrous continuous sheet and the first fibrous continuous sheet 4 come into contact with each other and are joined over the entire surface. In that case, one sheet 4(6) corresponds to the "fibrous continuous sheet" in the claims, and the other sheet 6(4) corresponds to the "article to be overlapped" in the claims. Moreover, the number of layers of the sheets 6, 4 is also not limited to two sheets, and three or more sheets may also be used. In the present aspect, that is, even in the case that the absorbent body 3 is not interposed, if the continuous sheet 6(4) that is either one of the upper and lower surfaces is a fibrous continuous sheet, the present invention can be applied thereto. Therefore, the sheet 4(6) other than the continuous sheet 6(4) that is the above-mentioned one of the surfaces need not be a fibrous sheet.

Figure 3:
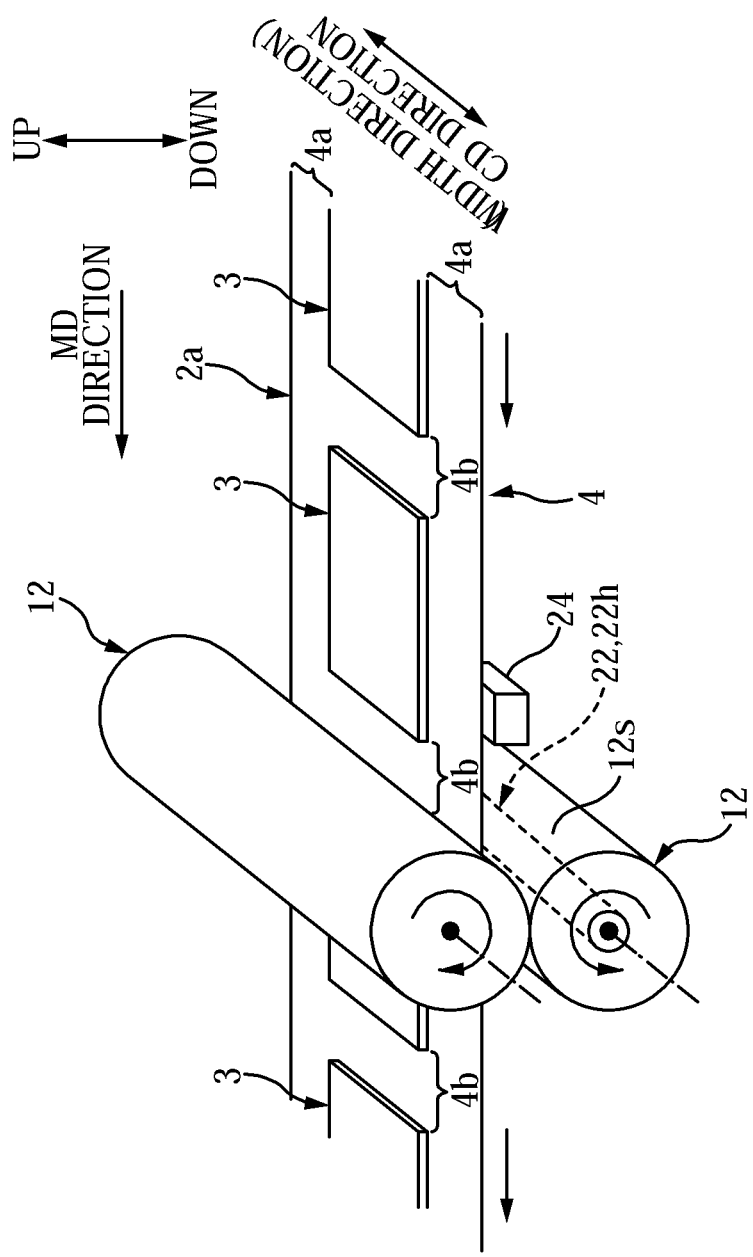
FIG. 3 is a perspective view of another aspect 2a of a semi-finished product 2.

Moreover, as shown in a perspective view of FIG. 3, a semi-finished product 2a can also be exemplified as another aspect 2a of the semi-finished product 2, in which only a plurality of absorbent bodies 3, 3 . . . , which are articles to be overlapped, adheres to one of the surfaces of the fibrous continuous sheet 4. More specifically, the fibrous continuous sheet 4 is provided only on the lower surface side of the absorbent body 3 and does not have to be provided on the upper surface side. In that case, in the fibrous continuous sheet 4, the hot-melt adhesive is selectively applied only to portions on which each absorbent body 3 is placed. It is needless to say that portions on which the absorbent body is not placed are not applied with the adhesive. For example, when the width of the fibrous continuous sheet 4 is larger than that of the absorbent body 3, and the fibrous continuous sheet 4 has a portion 4a that projects outside of the absorbent body 3 in the width direction, the hot-melt adhesive is not applied on the projected portion 4a. Furthermore, when the absorbent body 3 is not continuously placed in a strip-shape in the MD direction, but is placed intermittently in an island-shape in the MD direction as shown in FIG. 4, the hot-melt adhesive is also not applied on a portion 4b between the absorbent bodies 3, 3 in the fibrous continuous sheet 4.

In the semi-finished product 2a having such aspect, as shown in FIG. 3, the heating element 22 and the temperature sensor 24 are provided only for the lower press roller 12 that is a roller located on the side of the fibrous continuous sheet 4, and need not be provided for the upper press roller 12. This is because, it is considered there is little possibility of the oozing of the hot-melt adhesive to the upper surface of the absorbent body 3 since the absorbent body 3 generally has a high lamination density of fabric. However, in the case that the oozing to the upper surface is assumed to occur because of the low lamination density of the absorbent body 3, or the like, the heating element 22 and the temperature sensor 24 may be provided for the upper press roller 12.

Figure 4:
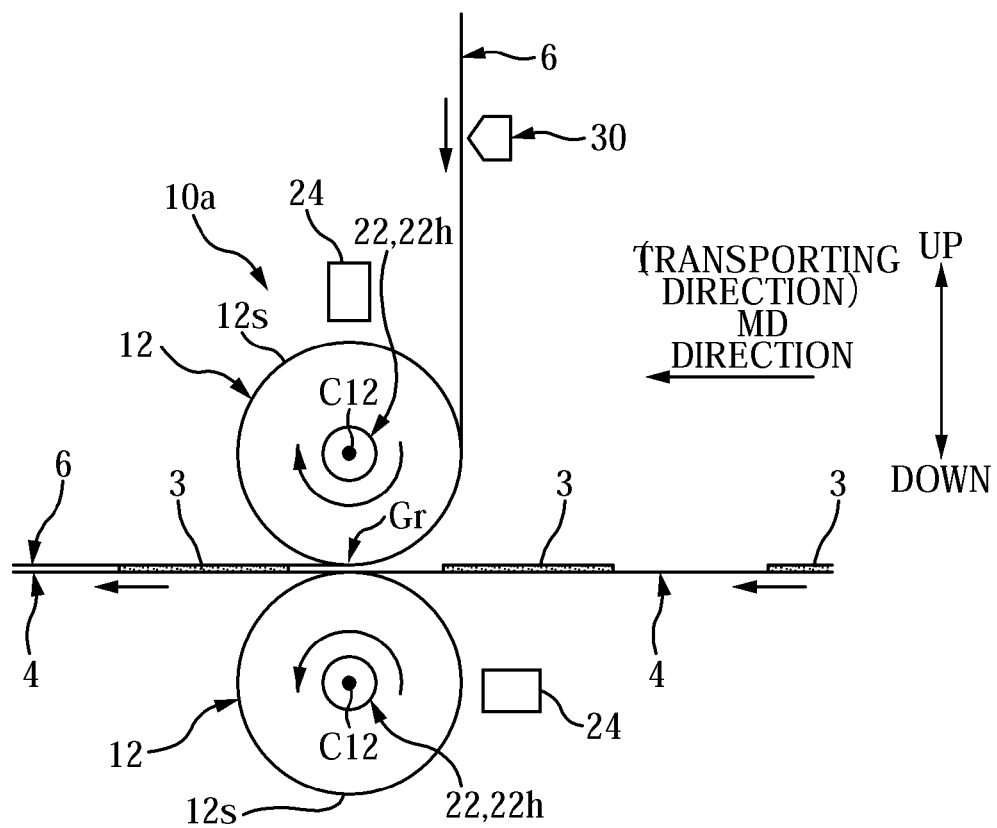
FIG. 4 is a schematic side view of a modified example 10a of the pressing apparatus 10.

FIG. 4 is a schematic side view of a modified example 10a of the pressing apparatus 10.

In the above-mentioned embodiment, a semi-finished product 2 is supplied to a pair of upper and lower press rollers 12, 12 in a state in which the second fibrous continuous sheet 6, the absorbent body 3, and the first fibrous continuous sheet 4 have been integrated and overlapped (FIG. 2A). On the other hand, in this modified example as shown in FIG. 4, the first fibrous continuous sheet 4 on which the absorbent body 3 is placed and the second fibrous continuous sheet 6 are separately supplied to a pair of upper and lower press rollers 12, 12 in a state in which each sheet is set apart from one another. At the roller gap Gr between the press rollers 12, 12, these continuous sheets 4, 6 are overlapped to be joined and integrated.

More specifically, the first fibrous continuous sheet 4 is transported to the press rollers 12, 12, for example, in the horizontal direction. On the other hand, the second fibrous continuous sheet 6 is transported to the press rollers 12, 12 along a transport path heading downward in the vertical direction. In this transport path, a hot-melt adhesive application device 30 is arranged. By this application device 30, the hot-melt adhesive is applied on a surface of the two surfaces of the continuous sheet 6, which is to face the absorbent body 3, over substantially the entire surface with a predetermined application pattern. Then, the continuous sheet 6 wraps around the outer circumferential surface 12s of the upper press roller 12 with a wrapping angle of substantially 90°, and is transported to the roller gap Gr in a integrated manner with the outer circumferential surface 12s. At the roller gap Gr, the continuous sheet 6 is overlapped on the upper surface of the first fibrous continuous sheet 4 from above. Thereby, the second fibrous continuous sheet 6 is joined to the first fibrous continuous sheet 4 so as to sandwich the absorbent body 3 between the first fibrous continuous sheet 4 and the second continuous sheet 6.

Note that, also in this modified example, in a similar manner to the above-mentioned embodiment, there is a possibility that the adhesive oozes out from the upper surface of the second fibrous continuous sheet 6 that is to come into contact with the outer circumferential surface 12s of the upper press roller 12. Furthermore, there is a possibility that the adhesive oozes out from the lower surface of the first fibrous continuous sheet 4 that is to come into contact with the outer circumferential surface 12s of the lower press roller 12. Therefore, the above-mentioned heating elements 22, 22 and the temperature sensors 24, 24 are provided for the pair of upper and lower press rollers 12, 12, respectively. Thereby, each of the temperatures of the outer circumferential surfaces 12s, 12s of the press rollers 12, 12 is kept within a range from 70° C. to 120° C.

Note that, since the other configurations are generally the same as those in the above-mentioned embodiment, structural components corresponding to those of the above-mentioned embodiment are denoted by the same reference characters in FIG. 4 and the detail descriptions thereof will be omitted.

Other Embodiments

While the embodiments of the present invention have been described as mentioned above, the present invention is not limited to such embodiments and can be altered as described below.

In the above-mentioned embodiment, as an example of a pair of upper and lower press rollers 12, 12, it has been described that both rollers 12, 12 are flat rollers in which the outer circumferential surfaces 12s, 12s thereof are smooth. However, the invention is not limited thereto. For example, one of the pair of upper and lower rollers may be an embossing roller having a plurality of convex sections that protrudes from the outer circumferential surface, and the other roller may be an anvil roller having a smooth outer circumferential surface that receives the convex sections. Or, both of the rollers may be embossing rollers.

In the foregoing embodiment, as an example of the absorbent article, disposable diapers worn by a wearer to absorb excreted fluid thereof have been given. However, the invention is not limited thereto as long as the article absorbs excreted fluid such as urine, menstrual blood, or the like. For example, sanitary napkins or pet sheets that absorb excreted fluid of pets may also be used.

In the above-mentioned embodiment, the configuration in which the electric heater was used for the heating element 22 of the heating mechanism was described. However, if it is possible to heat the press roller 12, the invention is not limited thereto. For example, an induction heating device may be used as the heating mechanism. That is, the induction heating device includes a dynamic magnetic field generating section that is arranged opposite the outer circumferential surface 12s of the press roller 12 in a non-contact state. When this dynamic magnetic field generating section generates a high-frequency dynamic magnetic field to the outer circumferential surface 12s, eddy currents occur on the outer circumferential surface 12s by the action of this dynamic magnetic field. Then, the outer circumferential surface 12s produces heat by the eddy currents, so that the outer circumferential surface 12s is heated. When this induction heating device is used, a roller made of a conductive material will be used for the press roller 12.

REFERENCE SIGNS LIST 2 semi-finished product, 2a semi-finished product,
3 absorbent body (article to be overlapped),
4 first fibrous continuous sheet (fibrous continuous sheet),
4a portion, 4b portion,
6 second fibrous continuous sheet (fibrous continuous sheet),
6a portion, 6b portion,
10 pressing apparatus, 10a pressing apparatus,
12 press roller, 12s outer circumferential surface,
22 heating element, 22h receiving hole, 24 temperature sensor,
30 adhesive application device,
Gr roller gap, C12 rotational shaft

The invention claimed is:

1. A method of pressing an absorbent article which comprises:
   providing an absorbent article comprising a fibrous continuous sheet, a fluid-impermeable continuous sheet and a plurality of absorbent bodies sandwiched between the fibrous continuous sheet and the fluid-impermeable continuous sheet with a thermoplastic adhesive;
   passing the absorbent article in a continuous direction of the fibrous continuous sheet through a roller gap between a pair of rollers that are driven and rotate with outer circumferential surfaces thereof facing each other, so that the fibrous continuous sheet, the fluid-impermeable continuous sheet and the plurality of absorbent articles are sandwiched and pressed between the outer circumferential surfaces of the pair of rollers;
   heating only one roller of the pair of rollers that is positioned on a side of the fibrous continuous sheet and contacts the fibrous continuous sheet so as to keep a temperature of the outer circumferential surface of the roller within a range from 70° C. to 120° C.; and
   wherein
   the thermoplastic adhesive is ejected from a nozzle of an adhesive application device between the fibrous continuous sheet and the article plurality of absorbent articles,
   the thermoplastic adhesive is made to be substantially in a cohesive state just before reaching the roller gap by making a temperature of the thermoplastic adhesive fall to 40° C. to 60° C. just before reaching the roller gap,
   the one roller of the pair of rollers that is positioned on a side of the fibrous continuous sheet is heated with a heating mechanism,
   the heating mechanism includes a heating element inserted in a receiving hole of the one roller,
   the receiving hole receives the heating element along a rotational shaft of the one roller and is formed so that a center of the receiving hole corresponds to the rotational shaft.

2. A method of pressing an absorbent article according to claim 1, wherein,
   the temperature of the outer circumferential surface of the only roller that contacts the fibrous continuous sheet is kept within a range from 80° C. to 110° C.

3. A method of pressing an absorbent article according to claim 1, wherein,
   the thermoplastic adhesive is a hot-melt adhesive, and
   the fibrous continuous sheet is tissue paper.

* * * * *